(12) United States Patent
O'Neil (10) Patent No.: US 10,433,974 B2
(45) Date of Patent: Oct. 8, 2019

(54) INTERVERTEBRAL IMPLANT WITH CONFORMABLE ENDPLATE

(71) Applicant: DePuy Synthes Products, Inc., Raynham, MA (US)

(72) Inventor: Michael J. O'Neil, West Barnstable, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/949,364

(22) Filed: Nov. 23, 2015

(65) Prior Publication Data

US 2016/0074175 A1 Mar. 17, 2016

Related U.S. Application Data

(60) Continuation of application No. 11/328,684, filed on Jan. 9, 2006, now abandoned, which is a division of
(Continued)

(51) Int. Cl.
| | |
|---|---|
| *A61F 2/44* | (2006.01) |
| *A61F 2/30* | (2006.01) |
| *A61F 2/28* | (2006.01) |

(52) U.S. Cl.
CPC ............ *A61F 2/4455* (2013.01); *A61F 2/442* (2013.01); *A61F 2/30767* (2013.01);
(Continued)

(58) Field of Classification Search
CPC .. A61F 2/44; A61F 2/441; A61F 2/442; A61F 2/4425; A61F 2/443; A61F 2/444
(Continued)

(56) References Cited

U.S. PATENT DOCUMENTS

| | | | |
|---|---|---|---|
| 3,855,638 A | | 12/1974 | Pilliar |
| 3,867,728 A | * | 2/1975 | Stubstad ................. A61F 2/441 |
| | | | 128/DIG. 21 |

(Continued)

FOREIGN PATENT DOCUMENTS

| | | |
|---|---|---|
| CN | 101909548 A | 12/2010 |
| DE | 28 04 936 A1 | 8/1979 |

(Continued)

OTHER PUBLICATIONS

Cheng, B.C., Ph.D., Biomechanical pullout strength and histology of Plasmapore® XP coated implants: Ovine multi point survival study. Aesculap Implant Systems, LLC, 2013, 12 pages.
(Continued)

*Primary Examiner* — Eduardo C Robert
*Assistant Examiner* — Michelle C Eckman
(74) *Attorney, Agent, or Firm* — Nutter McClennen & Fish LLP (57) ABSTRACT

The invention is generally related to an intervertebral implant for replacing an intervertebral disc of the human spine. The intervertebral implant includes a first conformable endplate, the first conformable endplate being conformable to a boney vertebral endplate under an anatomical load, a second endplate and a core between the endplates, wherein the first conformable endplate partitions the core from the boney vertebral endplate, whereby the core does not contact the boney vertebral endplate. The invention is also directed to a method of replacing an intervertebral disc. The method includes removing at least a portion of an intervertebral disc to form an intervertebral disc space, implanting a first conformable endplate, into the intervertebral disc space and in contact with a first boney vertebral endplate, the first conformable endplate being conformable to the first boney vertebral endplate under an anatomical load; implanting a
(Continued)

second endplate into the intervertebral disc space and in contact with a second boney vertebral endplate; and implanting a core between the first conformable endplate and the second endplate, wherein the first conformable endplate partitions the core from the first boney vertebral endplate, whereby the core does not contact the first boney vertebral endplate.

22 Claims, 8 Drawing Sheets

Related U.S. Application Data application No. 10/610,369, filed on Jun. 30, 2003, now abandoned.

(52) U.S. Cl.
CPC ..... *A61F 2/4425* (2013.01); *A61F 2002/2817* (2013.01); *A61F 2002/30014* (2013.01); *A61F 2002/30016* (2013.01); *A61F 2002/30616* (2013.01); *A61F 2002/30769* (2013.01); *A61F 2002/30841* (2013.01); *A61F 2002/30891* (2013.01); *A61F 2250/0018* (2013.01); *A61F 2250/0019* (2013.01); *A61F 2310/00017* (2013.01); *A61F 2310/00023* (2013.01); *A61F 2310/00029* (2013.01); *A61F 2310/00401* (2013.01); *A61F 2310/00407* (2013.01); *A61F 2310/00796* (2013.01); *A61F 2310/00976* (2013.01)

(58) Field of Classification Search
USPC .......................................... 623/17.11–17.16
See application file for complete search history.

(56) References Cited

U.S. PATENT DOCUMENTS

| | | | |
|---|---|---|---|
| 4,349,921 A * | 9/1982 | Kuntz | A61F 2/4425 623/17.16 |
| 4,351,069 A | 9/1982 | Ballintyn et al. | |
| 4,542,539 A | 9/1985 | Rowe, Jr. et al. | |
| 4,714,469 A | 12/1987 | Kenna | |
| 4,743,256 A | 5/1988 | Brantigan | |
| 4,759,766 A | 7/1988 | Buettner-Janz et al. | |
| 4,870,153 A | 9/1989 | Matzner et al. | |
| 4,871,366 A | 10/1989 | von Recum et al. | |
| 4,878,915 A | 11/1989 | Brantigan | |
| 4,911,718 A | 3/1990 | Lee et al. | |
| 4,932,969 A | 6/1990 | Frey et al. | |
| 4,946,378 A | 8/1990 | Hirayama et al. | |
| 5,030,233 A * | 7/1991 | Ducheyne | A61F 2/30907 623/23.54 |
| 5,071,437 A | 12/1991 | Steffee | |
| 5,123,926 A | 6/1992 | Pisharodi | |
| 5,134,477 A | 7/1992 | Knauer et al. | |
| 5,290,312 A | 3/1994 | Kojimoto et al. | |
| 5,306,307 A | 4/1994 | Senter et al. | |
| 5,306,308 A | 4/1994 | Gross et al. | |
| 5,306,309 A | 4/1994 | Wagner et al. | |
| 5,314,477 A | 5/1994 | Marnay | |
| 5,344,252 A | 9/1994 | Kakimoto | |
| 5,370,697 A | 12/1994 | Baumgartner | |
| 5,372,660 A | 12/1994 | Davidson et al. | |
| 5,374,267 A | 12/1994 | Siegal | |
| 5,401,269 A | 3/1995 | Buttner-Janz et al. | |
| 5,425,773 A | 6/1995 | Boyd et al. | |
| 5,458,641 A * | 10/1995 | Ramirez Jimenez | A61F 2/44 403/43 |
| 5,458,643 A | 10/1995 | Oka et al. | |
| 5,507,816 A | 4/1996 | Bullivant | |
| 5,514,180 A | 5/1996 | Heggeness et al. | |
| 5,534,029 A | 7/1996 | Shima | |
| 5,534,030 A | 7/1996 | Navarro et al. | |
| 5,554,191 A | 9/1996 | Lahille | |
| 5,556,431 A | 9/1996 | Buttner-Janz | |
| 5,562,738 A | 10/1996 | Boyd et al. | |
| 5,609,635 A | 3/1997 | Michelson | |
| 5,645,596 A | 7/1997 | Kim et al. | |
| 5,653,763 A | 8/1997 | Errico et al. | |
| 5,674,296 A | 10/1997 | Bryan et al. | |
| 5,676,701 A | 10/1997 | Yuan et al. | |
| 5,683,465 A | 11/1997 | Shinn et al. | |
| 5,697,977 A | 12/1997 | Pisharodi | |
| 5,702,450 A | 12/1997 | Bisserie et al. | |
| 5,716,415 A | 2/1998 | Steffee | |
| 5,755,798 A | 5/1998 | Papavero et al. | |
| 5,772,661 A | 6/1998 | Michelson | |
| 5,782,832 A | 7/1998 | Larsen et al. | |
| 5,824,094 A | 10/1998 | Serhan et al. | |
| 5,865,846 A | 2/1999 | Bryan et al. | |
| 5,888,224 A | 3/1999 | Beckers et al. | |
| 5,888,226 A | 3/1999 | Rogozinski | |
| 5,888,227 A | 3/1999 | Cottle | |
| 5,893,889 A | 4/1999 | Harrington | |
| 5,893,890 A | 4/1999 | Pisharodi | |
| 5,895,428 A | 4/1999 | Berry | |
| 5,980,522 A | 11/1999 | Koros et al. | |
| 5,989,291 A | 11/1999 | Ralph et al. | |
| 6,019,792 A | 2/2000 | Cauthen | |
| 6,022,350 A | 2/2000 | Ganem | |
| 6,039,761 A | 3/2000 | Li et al. | |
| 6,039,763 A | 3/2000 | Shelokov | |
| 6,045,579 A | 4/2000 | Hochshuler et al. | |
| 6,063,121 A | 5/2000 | Xavier et al. | |
| 6,099,531 A | 8/2000 | Bonutti | |
| 6,106,557 A | 8/2000 | Robioneck et al. | |
| 6,113,637 A | 9/2000 | Gill et al. | |
| 6,113,638 A | 9/2000 | Williams et al. | |
| 6,127,597 A | 10/2000 | Beyar et al. | |
| 6,136,031 A | 10/2000 | Middleton | |
| 6,139,579 A | 10/2000 | Steffee et al. | |
| 6,146,387 A | 11/2000 | Trott et al. | |
| 6,146,420 A | 11/2000 | McKay | |
| 6,146,421 A | 11/2000 | Gordon et al. | |
| 6,162,252 A | 12/2000 | Kuras et al. | |
| 6,179,794 B1 | 1/2001 | Burras | |
| 6,179,873 B1 | 1/2001 | Zientek | |
| 6,183,517 B1 | 2/2001 | Suddaby | |
| 6,197,065 B1 | 3/2001 | Martin et al. | |
| 6,241,769 B1 | 6/2001 | Nicholson et al. | |
| 6,296,647 B1 | 10/2001 | Robioneck et al. | |
| 6,302,914 B1 | 10/2001 | Michelson | |
| 6,332,895 B1 | 12/2001 | Suddaby | |
| 6,368,350 B1 | 4/2002 | Erickson et al. | |
| 6,375,681 B1 | 4/2002 | Truscott | |
| 6,409,766 B1 | 6/2002 | Brett | |
| 6,416,551 B1 | 7/2002 | Keller | |
| 6,419,706 B1 | 7/2002 | Graf | |
| 6,454,806 B1 | 9/2002 | Cohen et al. | |
| 6,468,310 B1 | 10/2002 | Ralph et al. | |
| 6,488,710 B2 | 12/2002 | Besselink | |
| 6,517,580 B1 | 2/2003 | Ramadan et al. | |
| 6,527,804 B1 | 3/2003 | Gauchet et al. | |
| 6,533,818 B1 | 3/2003 | Weber et al. | |
| 6,547,823 B2 | 4/2003 | Scarborough et al. | |
| 6,579,320 B1 | 6/2003 | Gauchet et al. | |
| 6,582,466 B1 | 6/2003 | Gauchet | |
| 6,582,467 B1 | 6/2003 | Teitelbaum et al. | |
| 6,582,468 B1 | 6/2003 | Gauchet | |
| 6,592,624 B1 | 7/2003 | Fraser et al. | |
| 6,607,558 B2 | 8/2003 | Kuras | |
| 6,626,943 B2 | 9/2003 | Eberlein et al. | |
| 6,641,614 B1 | 11/2003 | Wagner et al. | |
| 6,645,248 B2 | 11/2003 | Casutt | |
| 6,648,917 B2 | 11/2003 | Gerbec et al. | |
| 6,669,732 B2 | 12/2003 | Serhan et al. | |
| 6,676,665 B2 | 1/2004 | Foley et al. | |
| 6,682,562 B2 | 1/2004 | Viart et al. | |
| 6,706,070 B1 | 3/2004 | Wagner et al. | |
| 6,719,796 B2 | 4/2004 | Cohen et al. | |

(56) References Cited

U.S. PATENT DOCUMENTS

| | | |
|---|---|---|
| 6,723,126 B1 | 4/2004 | Berry |
| 6,723,127 B2 | 4/2004 | Ralph et al. |
| 6,733,532 B1 | 5/2004 | Gauchet et al. |
| 6,740,117 B2 | 5/2004 | Ralph et al. |
| 6,743,255 B2 | 6/2004 | Ferree |
| 6,758,861 B2 | 7/2004 | Ralph et al. |
| 6,758,862 B2 | 7/2004 | Berry et al. |
| 6,793,678 B2 | 9/2004 | Hawkins |
| 6,805,714 B2 | 10/2004 | Sutcliffe |
| 6,855,167 B2 | 2/2005 | Shimp et al. |
| 6,863,673 B2 | 3/2005 | Gerbec et al. |
| 6,881,229 B2 | 4/2005 | Khandkar et al. |
| 6,893,464 B2 | 5/2005 | Kiester |
| 6,936,071 B1 | 8/2005 | Marnay et al. |
| 6,953,477 B2 | 10/2005 | Berry |
| 6,955,691 B2 | 10/2005 | Chae et al. |
| 6,964,686 B2 | 11/2005 | Gordon |
| 6,966,910 B2 | 11/2005 | Ritland |
| 6,969,404 B2 | 11/2005 | Ferree |
| 7,018,412 B2 | 3/2006 | Ferreira et al. |
| 7,018,416 B2 | 3/2006 | Hanson et al. |
| 7,022,138 B2 | 4/2006 | Mashburn |
| 7,025,787 B2 | 4/2006 | Bryan et al. |
| 7,037,339 B2 | 5/2006 | Houfburg |
| 7,083,650 B2 | 8/2006 | Moskowitz et al. |
| 7,094,257 B2 | 8/2006 | Mujwid et al. |
| 7,156,876 B2 | 1/2007 | Moumene et al. |
| 7,211,112 B2 | 5/2007 | Baynham et al. |
| 7,217,293 B2 | 5/2007 | Branch, Jr. |
| 7,220,280 B2 | 5/2007 | Kast et al. |
| 7,223,292 B2 | 5/2007 | Messerli et al. |
| 7,226,483 B2 | 6/2007 | Gerber et al. |
| 7,235,101 B2 | 6/2007 | Berry et al. |
| 7,291,173 B2 | 11/2007 | Richelsoph et al. |
| 7,320,708 B1 | 1/2008 | Bernstein |
| 7,442,211 B2 | 10/2008 | de Villiers et al. |
| 7,503,920 B2 | 3/2009 | Siegal |
| 7,503,933 B2 | 3/2009 | Michelson |
| 7,507,241 B2 | 3/2009 | Levy et al. |
| 7,517,363 B2 | 4/2009 | Rogers et al. |
| 7,569,074 B2 | 8/2009 | Eisermann et al. |
| 7,575,599 B2 | 8/2009 | Villiers et al. |
| 7,618,458 B2 | 11/2009 | Biedermann et al. |
| 7,621,950 B1 | 11/2009 | Globerman et al. |
| 7,621,960 B2 | 11/2009 | Boyd et al. |
| 7,641,692 B2 | 1/2010 | Bryan et al. |
| 7,691,147 B2 | 4/2010 | Gutlin et al. |
| 7,722,612 B2 | 5/2010 | Sala et al. |
| 7,722,674 B1 | 5/2010 | Grotz |
| 7,744,650 B2 | 6/2010 | Lindner et al. |
| 7,749,270 B2 | 7/2010 | Peterman |
| 7,771,473 B2 | 8/2010 | Thramann |
| 7,789,914 B2 | 9/2010 | Michelson |
| 7,799,080 B2 | 9/2010 | Doty |
| 7,799,083 B2 | 9/2010 | Smith et al. |
| 7,819,921 B2 | 10/2010 | Grotz |
| 7,824,445 B2 | 11/2010 | Biro et al. |
| 7,846,206 B2 | 12/2010 | Oglaza et al. |
| 7,854,766 B2 | 12/2010 | Moskowitz et al. |
| 7,874,980 B2 | 1/2011 | Sonnenschein et al. |
| 7,879,098 B1 | 2/2011 | Simmons, Jr. |
| 7,887,589 B2 | 2/2011 | Glenn et al. |
| 7,909,870 B2 | 3/2011 | Kraus |
| 7,918,874 B2 | 4/2011 | Siegal |
| 7,922,729 B2 | 4/2011 | Michelson |
| 7,947,078 B2 | 5/2011 | Siegal |
| 7,951,199 B2 | 5/2011 | Miller |
| 7,959,675 B2 | 6/2011 | Gately |
| 7,985,231 B2 | 7/2011 | Sankaran |
| 7,993,403 B2 | 8/2011 | Foley et al. |
| 8,021,424 B2 | 9/2011 | Beger et al. |
| 8,021,426 B2 | 9/2011 | Segal et al. |
| 8,025,697 B2 | 9/2011 | McClellan, III et al. |
| 8,034,109 B2 | 10/2011 | Zwirkoski |
| 8,043,381 B2 | 10/2011 | Hestad et al. |
| 8,052,754 B2 | 11/2011 | Froehlich |
| 8,057,545 B2 | 11/2011 | Hughes et al. |
| 8,062,375 B2 | 11/2011 | Glerum et al. |
| 8,075,621 B2 | 12/2011 | Michelson |
| 8,097,036 B2 | 1/2012 | Cordaro et al. |
| 8,177,812 B2 | 5/2012 | Sankaran |
| 8,192,495 B2 | 6/2012 | Simpson et al. |
| 8,202,322 B2 | 6/2012 | Doty |
| 8,206,423 B2 | 6/2012 | Siegal |
| 8,216,312 B2 | 7/2012 | Gray |
| 8,216,314 B2 | 7/2012 | Richelsoph |
| 8,221,501 B2 | 7/2012 | Eisermann et al. |
| 8,221,502 B2 | 7/2012 | Branch, Jr. |
| 8,221,503 B2 | 7/2012 | Garcia et al. |
| 8,231,681 B2 | 7/2012 | Castleman et al. |
| 8,236,029 B2 | 8/2012 | Siegal |
| 8,236,058 B2 | 8/2012 | Fabian et al. |
| 8,241,328 B2 | 8/2012 | Siegal |
| 8,241,358 B2 | 8/2012 | Butler et al. |
| 8,241,361 B2 | 8/2012 | Link |
| 8,246,622 B2 | 8/2012 | Siegal et al. |
| 8,257,442 B2 | 9/2012 | Edie et al. |
| 8,262,666 B2 | 9/2012 | Baynham et al. |
| 8,267,939 B2 | 9/2012 | Cipoletti et al. |
| 8,267,965 B2 | 9/2012 | Gimbel et al. |
| 8,273,128 B2 | 9/2012 | Oh et al. |
| 8,287,599 B2 | 10/2012 | McGuckin, Jr. |
| 8,292,959 B2 | 10/2012 | Webb et al. |
| 8,303,663 B2 | 11/2012 | Jimenez et al. |
| 8,323,345 B2 | 12/2012 | Sledge |
| 8,328,812 B2 | 12/2012 | Siegal et al. |
| 8,328,852 B2 | 12/2012 | Zehavi et al. |
| 8,337,559 B2 | 12/2012 | Hansell et al. |
| 8,353,961 B2 | 1/2013 | McClintock et al. |
| 8,361,154 B2 | 1/2013 | Reo |
| 8,377,098 B2 | 2/2013 | Landry et al. |
| 8,398,712 B2 | 3/2013 | de Villiers et al. |
| 8,398,713 B2 | 3/2013 | Weiman |
| 8,409,290 B2 | 4/2013 | Zamani et al. |
| 8,409,291 B2 | 4/2013 | Blackwell et al. |
| 8,414,650 B2 | 4/2013 | Bertele et al. |
| 8,435,298 B2 | 5/2013 | Weiman |
| 8,454,698 B2 | 6/2013 | de Villiers et al. |
| 8,465,524 B2 | 6/2013 | Siegal |
| 8,480,715 B2 | 7/2013 | Gray |
| 8,480,742 B2 | 7/2013 | Pisharodi |
| 8,486,109 B2 | 7/2013 | Siegal |
| 8,486,148 B2 | 7/2013 | Butler et al. |
| 8,491,659 B2 | 7/2013 | Weiman |
| 8,506,635 B2 | 8/2013 | Palmatier et al. |
| 8,518,087 B2 | 8/2013 | Lopez et al. |
| 8,518,120 B2 | 8/2013 | Glerum et al. |
| 8,545,567 B1 | 10/2013 | Krueger |
| 8,551,173 B2 | 10/2013 | Lechmann et al. |
| 8,556,979 B2 | 10/2013 | Glerum et al. |
| 8,568,481 B2 | 10/2013 | Olmos et al. |
| 8,579,977 B2 | 11/2013 | Fabian |
| 8,591,585 B2 | 11/2013 | McLaughlin et al. |
| 8,597,330 B2 | 12/2013 | Siegal |
| 8,603,168 B2 | 12/2013 | Gordon et al. |
| 8,603,177 B2 | 12/2013 | Gray |
| 8,628,576 B2 | 1/2014 | Triplett et al. |
| 8,628,578 B2 | 1/2014 | Miller et al. |
| 8,632,595 B2 | 1/2014 | Weiman |
| 8,641,764 B2 | 2/2014 | Gately |
| 8,663,329 B2 | 3/2014 | Ernst |
| 8,668,740 B2 | 3/2014 | Rhoda et al. |
| 8,672,977 B2 | 3/2014 | Siegal et al. |
| 8,679,183 B2 | 3/2014 | Glerum et al. |
| 8,685,095 B2 | 4/2014 | Miller et al. |
| 8,685,098 B2 | 4/2014 | Glerum et al. |
| 8,696,751 B2 | 4/2014 | Ashley et al. |
| 8,709,086 B2 | 4/2014 | Glerum |
| 8,715,351 B1 | 5/2014 | Pinto |
| 8,721,723 B2 | 5/2014 | Hansell et al. |
| 8,728,166 B2 | 5/2014 | Schwab |
| 8,753,398 B2 | 6/2014 | Gordon et al. |
| 8,758,441 B2 | 6/2014 | Hovda et al. |
| 8,764,806 B2 | 7/2014 | Abdou |

(56) References Cited

U.S. PATENT DOCUMENTS

| | | |
|---|---|---|
| 8,771,360 B2 | 7/2014 | Jimenez et al. |
| 8,777,993 B2 | 7/2014 | Siegal et al. |
| 8,778,025 B2 | 7/2014 | Ragab et al. |
| 8,795,366 B2 | 8/2014 | Varela |
| 8,795,374 B2 | 8/2014 | Chee |
| 8,801,792 B2 | 8/2014 | de Villiers et al. |
| 8,828,085 B1 | 9/2014 | Jensen |
| 8,845,638 B2 | 9/2014 | Siegal et al. |
| 8,845,728 B1 | 9/2014 | Abdou |
| 8,845,731 B2 | 9/2014 | Weiman |
| 8,845,732 B2 | 9/2014 | Weiman |
| 8,852,279 B2 | 10/2014 | Weiman |
| 8,864,833 B2 | 10/2014 | Glerum et al. |
| 8,888,853 B2 | 11/2014 | Glerum et al. |
| 8,888,854 B2 | 11/2014 | Glerum et al. |
| 8,900,235 B2 | 12/2014 | Siegal |
| 8,900,307 B2 | 12/2014 | Hawkins et al. |
| 8,906,098 B2 | 12/2014 | Siegal |
| 8,936,641 B2 | 1/2015 | Cain |
| 8,940,052 B2 | 1/2015 | Lechmann et al. |
| 8,986,388 B2 | 3/2015 | Siegal et al. |
| 9,017,408 B2 | 4/2015 | Siegal et al. |
| 9,017,413 B2 | 4/2015 | Siegal et al. |
| 9,044,334 B2 | 6/2015 | Siegal et al. |
| 9,089,428 B2 | 7/2015 | Bertele et al. |
| 9,095,446 B2 | 8/2015 | Landry et al. |
| 9,095,447 B2 | 8/2015 | Barreiro et al. |
| 9,254,138 B2 | 2/2016 | Siegal et al. |
| 9,283,092 B2 | 3/2016 | Siegal et al. |
| 9,387,087 B2 | 7/2016 | Tyber |
| 9,408,712 B2 | 8/2016 | Siegal et al. |
| 9,414,923 B2 | 8/2016 | Studer et al. |
| 9,724,207 B2 | 8/2017 | DiMauro et al. |
| 9,925,060 B2 | 3/2018 | DiMauro et al. |
| 9,949,769 B2 | 4/2018 | Serhan et al. |
| 10,085,843 B2 | 10/2018 | DiMauro |
| 10,238,500 B2 | 3/2019 | Rogers et al. |
| 2001/0056302 A1* | 12/2001 | Boyer, II ............ B29C 43/006 623/17.15 |
| 2002/0010070 A1 | 1/2002 | Cales et al. |
| 2002/0029084 A1 | 3/2002 | Paul et al. |
| 2002/0032483 A1* | 3/2002 | Nicholson ......... A61B 17/1604 623/17.11 |
| 2002/0035400 A1 | 3/2002 | Bryan et al. |
| 2002/0037799 A1 | 3/2002 | Li et al. |
| 2002/0068976 A1 | 6/2002 | Jackson |
| 2002/0068977 A1 | 6/2002 | Jackson |
| 2002/0128715 A1 | 9/2002 | Bryan et al. |
| 2002/0128716 A1 | 9/2002 | Cohen et al. |
| 2002/0151976 A1 | 10/2002 | Foley et al. |
| 2002/0165612 A1 | 11/2002 | Gerber et al. |
| 2003/0004575 A1 | 1/2003 | Erickson |
| 2003/0004576 A1 | 1/2003 | Thalgott |
| 2003/0006942 A1 | 1/2003 | Searls et al. |
| 2003/0014112 A1* | 1/2003 | Ralph ................. A61F 2/4425 623/17.13 |
| 2003/0014116 A1 | 1/2003 | Ralph et al. |
| 2003/0023305 A1 | 1/2003 | McKay |
| 2003/0040799 A1 | 2/2003 | Boyd et al. |
| 2003/0045939 A1* | 3/2003 | Casutt ................. A61F 2/442 623/17.15 |
| 2003/0065396 A1 | 4/2003 | Michelson |
| 2003/0069642 A1 | 4/2003 | Ralph et al. |
| 2003/0078667 A1 | 4/2003 | Manasas et al. |
| 2003/0130739 A1 | 7/2003 | Gerbec et al. |
| 2003/0135275 A1* | 7/2003 | Garcia ................ A61B 17/025 623/17.11 |
| 2003/0139813 A1 | 7/2003 | Messerli et al. |
| 2003/0204261 A1 | 10/2003 | Eisermann et al. |
| 2003/0233145 A1 | 12/2003 | Landry et al. |
| 2004/0002761 A1 | 1/2004 | Rogers et al. |
| 2004/0010318 A1 | 1/2004 | Ferree |
| 2004/0024410 A1 | 2/2004 | Olson et al. |
| 2004/0030387 A1 | 2/2004 | Landry et al. |
| 2004/0064144 A1 | 4/2004 | Johnson et al. |
| 2004/0073310 A1 | 4/2004 | Moumene et al. |
| 2004/0088055 A1 | 5/2004 | Hanson et al. |
| 2004/0127991 A1 | 7/2004 | Ferree |
| 2004/0133279 A1 | 7/2004 | Krueger et al. |
| 2004/0143332 A1 | 7/2004 | Krueger et al. |
| 2004/0153065 A1 | 8/2004 | Lim |
| 2004/0153156 A1 | 8/2004 | Cohen et al. |
| 2004/0162618 A1 | 8/2004 | Mujwid et al. |
| 2004/0172133 A1 | 9/2004 | Gerber et al. |
| 2004/0186570 A1 | 9/2004 | Rapp |
| 2004/0186577 A1 | 9/2004 | Ferree |
| 2004/0193277 A1 | 9/2004 | Long et al. |
| 2004/0230309 A1 | 11/2004 | DiMauro et al. |
| 2004/0267367 A1 | 12/2004 | O'Neil |
| 2005/0019365 A1 | 1/2005 | Frauchiger et al. |
| 2005/0038515 A1 | 2/2005 | Kunzler |
| 2005/0113916 A1 | 5/2005 | Branch |
| 2005/0113917 A1 | 5/2005 | Chae et al. |
| 2005/0125062 A1 | 6/2005 | Biedermann et al. |
| 2005/0165485 A1 | 7/2005 | Trieu |
| 2005/0197702 A1* | 9/2005 | Coppes ................ A61F 2/441 623/17.12 |
| 2005/0222681 A1 | 10/2005 | Richley et al. |
| 2005/0256576 A1 | 11/2005 | Moskowitz et al. |
| 2005/0261769 A1 | 11/2005 | Moskowitz et al. |
| 2005/0278026 A1 | 12/2005 | Gordon et al. |
| 2006/0036241 A1 | 2/2006 | Siegal |
| 2006/0058876 A1 | 3/2006 | McKinley |
| 2006/0058880 A1 | 3/2006 | Wysocki et al. |
| 2006/0100706 A1 | 5/2006 | Shadduck et al. |
| 2006/0111785 A1 | 5/2006 | O'Neil |
| 2006/0122703 A1 | 6/2006 | Aebi et al. |
| 2006/0136062 A1 | 6/2006 | DiNello et al. |
| 2006/0206207 A1 | 9/2006 | Dryer et al. |
| 2006/0235531 A1 | 10/2006 | Buettner-Danz |
| 2006/0253201 A1 | 11/2006 | McLuen |
| 2006/0265075 A1 | 11/2006 | Baumgartner et al. |
| 2006/0265077 A1 | 11/2006 | Zwirkoski |
| 2006/0293753 A1 | 12/2006 | Thramann |
| 2007/0010886 A1 | 1/2007 | Banick et al. |
| 2007/0055377 A1 | 3/2007 | Hanson et al. |
| 2007/0118222 A1 | 5/2007 | Lang |
| 2007/0149978 A1 | 6/2007 | Shezifi et al. |
| 2007/0173939 A1 | 7/2007 | Kim et al. |
| 2007/0173940 A1 | 7/2007 | Hestad et al. |
| 2007/0178222 A1 | 8/2007 | Storey et al. |
| 2007/0191959 A1 | 8/2007 | Hartmann et al. |
| 2007/0198089 A1 | 8/2007 | Moskowitz et al. |
| 2007/0208423 A1 | 9/2007 | Messerli et al. |
| 2007/0219634 A1 | 9/2007 | Greenhalgh et al. |
| 2007/0233244 A1 | 10/2007 | Lopez et al. |
| 2007/0270968 A1 | 11/2007 | Baynham et al. |
| 2007/0276375 A1 | 11/2007 | Rapp |
| 2007/0299521 A1 | 12/2007 | Glenn et al. |
| 2008/0009877 A1 | 1/2008 | Sankaran et al. |
| 2008/0015701 A1 | 1/2008 | Garcia et al. |
| 2008/0021556 A1 | 1/2008 | Edie |
| 2008/0021558 A1 | 1/2008 | Thramann |
| 2008/0027550 A1 | 1/2008 | Link et al. |
| 2008/0033440 A1 | 2/2008 | Moskowitz et al. |
| 2008/0051902 A1 | 2/2008 | Dwyer |
| 2008/0058944 A1 | 3/2008 | Duplessis et al. |
| 2008/0065219 A1 | 3/2008 | Dye |
| 2008/0082173 A1 | 4/2008 | Delurio et al. |
| 2008/0132934 A1 | 6/2008 | Reiley et al. |
| 2008/0133017 A1 | 6/2008 | Beyar et al. |
| 2008/0140085 A1 | 6/2008 | Gately et al. |
| 2008/0140207 A1 | 6/2008 | Olmos et al. |
| 2008/0147193 A1 | 6/2008 | Matthis et al. |
| 2008/0161927 A1 | 7/2008 | Savage et al. |
| 2008/0167657 A1 | 7/2008 | Greenhalgh |
| 2008/0177388 A1 | 7/2008 | Patterson et al. |
| 2008/0183204 A1 | 7/2008 | Greenhalgh et al. |
| 2008/0195209 A1 | 8/2008 | Garcia et al. |
| 2008/0228225 A1 | 9/2008 | Trautwein et al. |
| 2008/0243251 A1 | 10/2008 | Stad et al. |
| 2008/0243254 A1 | 10/2008 | Butler |
| 2008/0249622 A1 | 10/2008 | Gray |

(56) References Cited

U.S. PATENT DOCUMENTS

| | | |
|---|---|---|
| 2008/0281425 A1 | 11/2008 | Thalgott et al. |
| 2009/0005873 A1 | 1/2009 | Slivka et al. |
| 2009/0030423 A1 | 1/2009 | Puno |
| 2009/0054991 A1 | 2/2009 | Biyani et al. |
| 2009/0069895 A1 | 3/2009 | Gittings et al. |
| 2009/0076610 A1 | 3/2009 | Afzal |
| 2009/0099568 A1 | 4/2009 | Lowry et al. |
| 2009/0112320 A1 | 4/2009 | Kraus |
| 2009/0112324 A1 | 4/2009 | Refai et al. |
| 2009/0164020 A1 | 6/2009 | Janowski et al. |
| 2009/0177281 A1 | 7/2009 | Swanson et al. |
| 2009/0177284 A1 | 7/2009 | Rogers et al. |
| 2009/0222096 A1 | 9/2009 | Trieu |
| 2009/0222099 A1 | 9/2009 | Liu et al. |
| 2009/0234398 A1 | 9/2009 | Chirico et al. |
| 2009/0240335 A1 | 9/2009 | Arcenio et al. |
| 2009/0248159 A1 | 10/2009 | Aflatoon |
| 2009/0248163 A1 | 10/2009 | King et al. |
| 2009/0276051 A1 | 11/2009 | Arramon et al. |
| 2009/0292361 A1 | 11/2009 | Lopez |
| 2010/0016905 A1 | 1/2010 | Greenhalgh et al. |
| 2010/0042218 A1 | 2/2010 | Nebosky et al. |
| 2010/0076559 A1 | 3/2010 | Bagga et al. |
| 2010/0094426 A1 | 4/2010 | Grohowski, Jr. et al. |
| 2010/0179594 A1 | 7/2010 | Theofilos et al. |
| 2010/0211182 A1 | 8/2010 | Zimmermann |
| 2010/0234956 A1 | 9/2010 | Attia et al. |
| 2010/0262240 A1 | 10/2010 | Chavatte et al. |
| 2010/0286783 A1 | 11/2010 | Lechmann et al. |
| 2010/0324607 A1 | 12/2010 | Davis |
| 2011/0004308 A1 | 1/2011 | Marino et al. |
| 2011/0004310 A1 | 1/2011 | Michelson |
| 2011/0015747 A1 | 1/2011 | McManus et al. |
| 2011/0029082 A1 | 2/2011 | Hall |
| 2011/0035011 A1 | 2/2011 | Cain |
| 2011/0082552 A1 | 4/2011 | Wistrom et al. |
| 2011/0093074 A1 | 4/2011 | Glerum et al. |
| 2011/0093076 A1 | 4/2011 | Reo et al. |
| 2011/0130835 A1 | 6/2011 | Ashley et al. |
| 2011/0130838 A1 | 6/2011 | Morgenstern Lopez |
| 2011/0144753 A1 | 6/2011 | Marchek et al. |
| 2011/0159070 A1 | 6/2011 | Jin et al. |
| 2011/0172716 A1 | 7/2011 | Glerum |
| 2011/0270261 A1 | 11/2011 | Mast et al. |
| 2011/0282453 A1 | 11/2011 | Greenhalgh et al. |
| 2011/0301711 A1 | 12/2011 | Palmatier et al. |
| 2011/0301712 A1 | 12/2011 | Palmatier et al. |
| 2012/0004726 A1 | 1/2012 | Greenhalgh et al. |
| 2012/0004732 A1 | 1/2012 | Goel et al. |
| 2012/0022654 A1 | 1/2012 | Farris et al. |
| 2012/0029636 A1 | 2/2012 | Ragab et al. |
| 2012/0071977 A1 | 3/2012 | Oglaza et al. |
| 2012/0071980 A1 | 3/2012 | Purcell et al. |
| 2012/0083889 A1 | 4/2012 | Purcell et al. |
| 2012/0123546 A1 | 5/2012 | Medina |
| 2012/0136443 A1 | 5/2012 | Wenzel |
| 2012/0197403 A1 | 8/2012 | Merves |
| 2012/0226357 A1 | 9/2012 | Varela |
| 2012/0277869 A1 | 11/2012 | Siccardi et al. |
| 2012/0290097 A1 | 11/2012 | Cipoletti et al. |
| 2012/0310350 A1 | 12/2012 | Farris et al. |
| 2013/0030536 A1 | 1/2013 | Rhoda et al. |
| 2013/0030544 A1 | 1/2013 | Studer |
| 2013/0060337 A1 | 3/2013 | Petersheim et al. |
| 2013/0073044 A1 | 3/2013 | Gamache |
| 2013/0085572 A1 | 4/2013 | Glerum et al. |
| 2013/0085574 A1 | 4/2013 | Sledge |
| 2013/0110240 A1 | 5/2013 | Hansell et al. |
| 2013/0116791 A1 | 5/2013 | Theofilos |
| 2013/0123924 A1 | 5/2013 | Butler et al. |
| 2013/0123927 A1 | 5/2013 | Malandain |
| 2013/0138214 A1 | 5/2013 | Greenhalgh et al. |
| 2013/0144387 A1 | 6/2013 | Walker et al. |
| 2013/0144388 A1 | 6/2013 | Emery et al. |
| 2013/0158663 A1 | 6/2013 | Miller et al. |
| 2013/0158664 A1 | 6/2013 | Palmatier et al. |
| 2013/0158667 A1 | 6/2013 | Tabor et al. |
| 2013/0158668 A1 | 6/2013 | Nichols et al. |
| 2013/0158669 A1 | 6/2013 | Sungarian et al. |
| 2013/0173004 A1 | 7/2013 | Greenhalgh et al. |
| 2013/0190876 A1 | 7/2013 | Drochner et al. |
| 2013/0190877 A1 | 7/2013 | Medina |
| 2013/0204371 A1 | 8/2013 | McLuen et al. |
| 2013/0211525 A1 | 8/2013 | McLuen et al. |
| 2013/0211526 A1 | 8/2013 | Alheidt et al. |
| 2013/0218276 A1 | 8/2013 | Fiechter et al. |
| 2013/0253585 A1 | 9/2013 | Garcia et al. |
| 2013/0261746 A1 | 10/2013 | Linares et al. |
| 2013/0310939 A1 | 11/2013 | Fabian et al. |
| 2014/0039622 A1 | 2/2014 | Glerum et al. |
| 2014/0046333 A1 | 2/2014 | Johnson et al. |
| 2014/0058513 A1 | 2/2014 | Gahman et al. |
| 2014/0067073 A1 | 3/2014 | Hauck |
| 2014/0086962 A1 | 3/2014 | Jin et al. |
| 2014/0114414 A1 | 4/2014 | Abdou et al. |
| 2014/0114423 A1 | 4/2014 | Suedkamp et al. |
| 2014/0128977 A1 | 5/2014 | Glerum et al. |
| 2014/0128980 A1 | 5/2014 | Kirschman |
| 2014/0135934 A1 | 5/2014 | Hansell et al. |
| 2014/0142706 A1 | 5/2014 | Hansell et al. |
| 2014/0163683 A1 | 6/2014 | Seifert et al. |
| 2014/0172106 A1 | 6/2014 | To et al. |
| 2014/0180421 A1 | 6/2014 | Glerum et al. |
| 2014/0188225 A1 | 7/2014 | Dmuschewsky |
| 2014/0249629 A1 | 9/2014 | Moskowitz et al. |
| 2014/0249630 A1 | 9/2014 | Weiman |
| 2014/0257484 A1 | 9/2014 | Flower et al. |
| 2014/0257486 A1 | 9/2014 | Alheidt |
| 2014/0257494 A1 | 9/2014 | Thorwarth et al. |
| 2014/0277476 A1 | 9/2014 | McLean et al. |
| 2014/0303731 A1 | 10/2014 | Glerum |
| 2014/0303732 A1 | 10/2014 | Rhoda et al. |
| 2014/0324171 A1 | 10/2014 | Glerum et al. |
| 2015/0088256 A1 | 3/2015 | Ballard |
| 2015/0238324 A1 | 8/2015 | Nebosky et al. |
| 2016/0038301 A1 | 2/2016 | Wickham |
| 2016/0058573 A1 | 3/2016 | DiMauro et al. |
| 2016/0067055 A1 | 3/2016 | Hawkins et al. |
| 2016/0074170 A1 | 3/2016 | Rogers et al. |
| 2016/0100954 A1 | 4/2016 | Rumi et al. |
| 2016/0128843 A1 | 5/2016 | Tsau et al. |
| 2016/0317714 A1 | 11/2016 | DiMauro et al. |
| 2017/0304074 A1 | 10/2017 | DiMauro et al. |
| 2018/0055649 A1 | 3/2018 | Kelly et al. |
| 2018/0078379 A1 | 3/2018 | Serhan et al. |
| 2019/0083276 A1 | 3/2019 | DiMauro |
| 2019/0105171 A1 | 4/2019 | Rogers et al. |

FOREIGN PATENT DOCUMENTS

| | | |
|---|---|---|
| DE | 39 11 610 A1 | 10/1990 |
| DE | 40 12 622 C1 | 7/1991 |
| DE | 20 2008 001 079 U1 | 3/2008 |
| EP | 0 282 161 A1 | 9/1988 |
| EP | 0 678 489 A1 | 10/1995 |
| EP | 1 290 985 A2 | 3/2003 |
| EP | 1 385 449 A2 | 2/2004 |
| EP | 1 532 949 A1 | 5/2005 |
| EP | 1 541 096 A1 | 6/2005 |
| EP | 1 385 449 B1 | 7/2006 |
| EP | 1 683 593 A2 | 7/2006 |
| EP | 1 698 305 B1 | 8/2007 |
| EP | 1 843 723 B1 | 3/2010 |
| EP | 2 368 529 A1 | 9/2011 |
| EP | 2 237 748 B1 | 9/2012 |
| EP | 2 641 571 A1 | 9/2013 |
| EP | 2 764 851 A1 | 8/2014 |
| FR | 2 718 635 A1 | 10/1995 |
| FR | 2 730 159 A1 | 8/1996 |
| FR | 2874814 A1 | 3/2006 |
| JP | 2003-526457 A | 9/2003 |
| JP | 2006-516456 A | 7/2006 |
| JP | 2011-509766 A | 3/2011 |
| WO | 94/04100 A1 | 3/1994 |

(56) References Cited

FOREIGN PATENT DOCUMENTS

| | | |
|---|---|---|
| WO | 95/31158 A1 | 11/1995 |
| WO | 97/00054 A1 | 1/1997 |
| WO | 99/53871 A1 | 10/1999 |
| WO | 00/13620 A1 | 3/2000 |
| WO | 00/53127 A1 | 9/2000 |
| WO | 01/01893 A1 | 1/2001 |
| WO | 01/01895 A1 | 1/2001 |
| WO | 01/17464 A1 | 3/2001 |
| WO | 2005/039455 A1 | 5/2005 |
| WO | 2005/112834 A2 | 12/2005 |
| WO | 2006/047587 A2 | 5/2006 |
| WO | 2006/058281 A2 | 6/2006 |
| WO | 2006/065419 A2 | 6/2006 |
| WO | 2006/081843 A1 | 8/2006 |
| WO | 2007/009107 A2 | 1/2007 |
| WO | 2007/028098 A2 | 3/2007 |
| WO | 2007/048012 A2 | 4/2007 |
| WO | 2007/084427 A2 | 7/2007 |
| WO | 2008/044057 A1 | 4/2008 |
| WO | 2009/064787 A2 | 5/2009 |
| WO | 2009/092102 A1 | 7/2009 |
| WO | 2009/124269 A1 | 10/2009 |
| WO | 2009/143496 A1 | 11/2009 |
| WO | 2010/068725 A2 | 6/2010 |
| WO | 2010/088766 A1 | 8/2010 |
| WO | 2010/148112 A1 | 12/2010 |
| WO | 2011/046459 A1 | 4/2011 |
| WO | 2011/046460 A1 | 4/2011 |
| WO | 2011/119617 A1 | 9/2011 |
| WO | 2011/142761 A1 | 11/2011 |
| WO | 2012/009152 A1 | 1/2012 |
| WO | 2012/028182 A1 | 3/2012 |
| WO | 2012/030331 A1 | 3/2012 |
| WO | 2012/089317 A1 | 7/2012 |
| WO | 2012/135764 A1 | 10/2012 |
| WO | 2013/006669 A2 | 1/2013 |
| WO | 2013/023096 A1 | 2/2013 |
| WO | 2013/025876 A1 | 2/2013 |
| WO | 2013/043850 A2 | 3/2013 |
| WO | 2013/082184 A1 | 6/2013 |
| WO | 2013/158294 A1 | 10/2013 |
| WO | 2013/173767 A1 | 11/2013 |
| WO | 2013/184946 A1 | 12/2013 |
| WO | 2014/014610 A1 | 1/2014 |
| WO | 2014/018098 A1 | 1/2014 |
| WO | 2014/026007 A1 | 2/2014 |
| WO | 2014/035962 A1 | 3/2014 |
| WO | 2014/088521 A2 | 6/2014 |
| WO | 2014/116891 A1 | 7/2014 |
| WO | 2015/048997 A1 | 4/2015 |

OTHER PUBLICATIONS

Kotsias, A., Clinical trial of titanium-coated PEEL cages anterior cervical discectomy and fusion. [Klinishe Untersuching zum Einsatz von titanbeschichteten Polyetheretherketon-Implantaten bei der cervikalen interkorporalen fusion]. Doctoral thesis. Department of Medicine, Charite, University of Medicine Berlin, 2014, 73 pages. (German language document/Engl. summary).
[No Author Listed] Link SB Charite—Intervertebral Prosthesis, Brochure, Waldemar Link GmbH & Co., 1988, 29 pages.
[No Author Listed] Porocoat® Porous Coating, Depuy Synthes Companies, 2015, 2 pages, webpage, accessed Jul. 5, 2016, <https://emea.depuysynthes.com/hcp/hip/products/qs/porocoat-porous-coating-emea>.
[No Author Listed] Spine Solutions—The non-fusion technology company, Brochure, Prodisc, Spine Solutions, Inc., 2001, 16 pages.
Chiang, et al., Biomechanical Comparison of Instrumented Posterior Lumbar Interbody Fusion with One or Two Cages by Finite Element Analysis, Spine, 2006, pp. E682-E689, vol. 31 (19), Lippincott Williams & Wilkins, Inc.
European Search Report EP03253921.5, dated Nov. 13, 2003, 4 pages.
Folman, et al., Posterior Lumbar Interbody Fusion for Degenerative Disc Disease Using a Minimally Invasive B-Twin Expandable Spinal Spacer, Journal of Spinal Disorders & Techniques, 2003, pp. 455-460, vol. 16(5).
Gore, Technique of Cervical Interbody Fusion, Clinical Orthopaedics and Related Research, 1984, pp. 191-195, No. 188.
Hoogland, T., et al., Total Lumbar Intervertebral Disc Replacement: Testing of a New Articulating Space in Human Cadaver Spines—24th Annual ORS, Dallas, TX, Feb. 21-23, 1978, 8 pages.
Hunt, et al., Expandable cage placement via a posterolateral approach in lumbar spine reconstructions, Journal of Neurosurgery: Spine, 2006, pp. 271-274, vol. 5.
International Patent Application No. PCT /US2013/029014, International Search Report dated Jul. 1, 2013, 2 pages.
Krbec, et al., [Replacement of the vertebral body with an expansion implant (Synex)], Acta Chir Orthop Traumatol Cech, 2002, pp. 158-162, vol. 69(3). Article in Czech. English Abstract Only.
Polikeit, et al., The importance of the end plate for interbody cages in the lumbar spine, Eur Spine J, 2003, pp. 556-561, vol. 12.
Shin, et al., Posterior Lumbar Interbody Fusion via a Unilateral Approach, Yonsei Medical Journal, 2006, pp. 319-325, vol. 47(3).
[No Author Listed] Porocoat® Porous Coating, Depuy Synthes Companies, 2017, 1 page, webpage, accessed Jul. 31, 2017, <https://emea.depuysynthes.com/hcp/hip/products/qs/porocoat-porous-coating-emea>.
Ha, S. W. et al., Topographical characterization and microstructural interface analysis of vacuum-plasma-sprayed titanium and hydroxyapatite coatings on carbon fibre-reinforced poly(etheretherketone), J. Mater. Sci.: Materials in Medicine, 1997, v. 8, pp. 891-896.
Harsha, A. P. et al, "Tribo performance of polyaryletherketone composites," Polymer Testing, 2002, v. 21, pp. 697-709.
Nguyen, H. X., et al, "Poly(Aryl-Ether-Ether-Ketone) and Its Advanced Composites: A Review," Polymer Composites, Apr. 1987, v. 8, p. 57.

* cited by examiner

INTERVERTEBRAL IMPLANT WITH CONFORMABLE ENDPLATE

CROSS-REFERENCE TO RELATED APPLICATIONS

This application is a continuation of U.S. patent application Ser. No. 11/328,684 filed on Jan. 9, 2006, which is a division of U.S. patent application Ser. No. 10/610,369 filed on Jun. 30, 2003, each of which is hereby incorporated herein by reference in its entirety.

BACKGROUND OF THE INVENTION

A human intervertebral disc has several important functions, including functioning as a spacer, a shock absorber, and a motion unit. In particular, the disc maintains the separation distance between adjacent boney vertebral bodies. The separation distance allows motion to occur, with the cumulative effect of each spinal segment yielding the total range of motion of the spine in several directions. Proper spacing is important because it allows the intervertebral foramen to maintain its height, which allows the segmental nerve roots room to exit each spinal level without compression. Further, the disc allows the spine to compress and rebound when the spine is axially loaded during such activities as jumping and running. Importantly, it also resists the downward pull of gravity on the head and trunk during prolonged sitting and standing. Furthermore, the disc allows the spinal segment to flex, rotate, and bend to the side, all at the same time during a particular activity. This would be impossible if each spinal segment were locked into a single axis of motion.

An unhealthy disc may result in pain. One way a disc may become unhealthy is when the inner nucleus dehydrates. This results in a narrowing of the disc space and a bulging of the annular ligaments. With progressive nuclear dehydration, the annular fibers can crack and tear. Further, loss of normal soft tissue tension may allow for a partial dislocation of the joint, leading to bone spurs, foraminal narrowing, mechanical instability, and pain.

Lumbar disc disease can cause pain and other symptoms in at least two ways. First, if the annular fibers stretch or rupture, the nuclear material may bulge or herniate and compress neural tissues resulting in leg pain and weakness. This condition is often referred to as a pinched nerve, slipped disc, or herniated disc. This condition typically will cause sciatica or radiating leg pain, as a result of mechanical and/or chemical irritation against the nerve root. Although the overwhelming majority of patients with a herniated disc and sciatica heal without surgery, if surgery is indicated it is generally a decompressive removal of the portion of herniated disc material, such as a discectomy or microdiscectomy.

Second, mechanical dysfunction can cause disc degeneration and pain (e.g. degenerative disc disease). For example, the disc may be damaged as the result of some trauma that overloads the capacity of the disc to withstand increased forces passing through it, and inner or outer portions of the annular fibers may tear. These torn fibers may be the focus for inflammatory response when they are subjected to increased stress, and may cause pain directly, or through the compensatory protective spasm of the deep paraspinal muscles.

Traditionally, spinal fusion surgery has been the treatment of choice for individuals who have not found pain relief for chronic back pain through conservative treatment (such as physical therapy, medication, manual manipulation, etc), and have remained disabled from their occupation, from their activities of daily living, or simply from enjoying a relatively pain-free day-to-day existence. There have been significant advances in spinal fusion devices and surgical techniques. However, the procedures generally include shaping two adjacent boney vertebral endplates to conform to the endplates of the fusion device. The removal of bone from the endplates weakens the vertebral bodies and can lead to device stress shielding, bone remodeling, device subsidence, and device expulsion. Further, known endplates can lead to uneven distribution of loads across the vertebral bodies.

Known artificial discs offers several theoretical benefits over spinal fusion for chronic back pain, including pain reduction and a potential to avoid premature degeneration at adjacent levels of the spine by maintaining normal spinal motion. However, like spinal fusion surgery, the removal of bone from the vertebral endplates typically is necessary, thereby, weakening the vertebral bodies. Further, known endplates cause uneven distribution of loads across the vertebral bodies.

Therefore, a need exists for an intervertebral implant and a method replacing an artificial disc that overcomes or minimizes the above-referenced problems.

SUMMARY OF THE INVENTION

The invention is generally related to an intervertebral implant for replacing an intervertebral disc of the human spine. The intervertebral implant includes a first conformable endplate, the first conformable endplate being conformable to a boney vertebral endplate under an anatomical load, a second endplate and a core between the endplates, wherein the first conformable endplate partitions the core from the boney vertebral endplate, whereby the core does not contact the boney vertebral endplate. The implant can be an artificial disc or a fusion cage.

In one embodiment of the invention, the second endplate is conformable to a second boney vertebral endplate under an anatomical load. Further, the second endplate partitions the core from the second boney vertebral endplate, whereby the core does not contact the second boney vertebral endplate.

In one embodiment of the invention, at least one rigid plate can be disposed between at least one of the first and second endplates and the core, the rigid plate including a material which does not deform under the anatomical load.

In one embodiment of invention, the first and second endplate can include a textured surface that facilitates bone growth. The textured surface can include at least one member selected from the group consisting of porous beading, hydroxyapatite, and mesh. Optionally, the textured surface can be treated with an osteoinductive material. The osteoinductive material includes at least one member selected from the group consisting of a metallic, a polymeric, a ceramic, and a biologic material. The metallic material includes at least one member selected from the group consisting of titanium, cobalt-chromium, nitinol, and stainless steel. The polymeric material includes at least one member selected from the group consisting of polyethylene, polyester, polyurethane, silicone, and polycarbonate. The ceramic material includes at least one member selected from the group consisting of zirconia, alumina, hydroxyapatite, and tricalcium phosphate. The biologic material includes at least one member selected from the group consisting of collagen, bone morphogenic protein, a demineralized bone matrix, and a growth factor.

At least one protrusion element can be optionally coupled to a surface of at least one of the first and second endplates, the protrusion element being capable of penetrating a boney vertebral endplate, thereby securing a position of the first or second endplate to the boney vertebral endplate. The protrusion element includes at least one member selected from the group consisting of a keel, a spike, a tooth, a fin, and a peg.

In one embodiment of the invention, the conformable material includes at least one member selected from the group consisting of a metallic, a polymeric, and a biologic material.

In one embodiment of the invention, the core between the endplates, the core supporting boney vertebral endplates between which the conformable endplates have been placed and wherein the position of each conformable endplate is controlled at least in part by the boney vertebral endplate to which it is attached and is independent of the position of the other endplate. Optionally, the core can be a non-fluid or the core can include an osteoinductive rigid matrix which provides for spinal fusion.

In one embodiment of the invention, a kit includes at least two first conformable endplates. Each first conformable endplate is conformable to a boney vertebral endplate under an anatomical load. Each first conformable endplate has at least one dimension that is distinct from another conformable endplate of the kit. Each second endplate has at least one dimension that is distinct from another second endplate of the kit. A core is dimensioned for implantation between a first conformable endplate and a second endplate in an intervertebral space that has been prepared for placement of the first conformable endplate, the second endplate and the core. Upon implantation, the first conformable endplate partitions the core from a first boney vertebral endplate with which the first conformable endplate is in contact, whereby the core does not contact the first boney vertebral endplate.

In one embodiment of the invention, the second endplate is conformable to a second boney vertebral endplate under an anatomical load. Further, upon implantation of the second endplate and the core into an intervertebral space that has been prepared for placement of the first conformable endplate, the core and the second endplate, the second endplate partitions the core from the second honey vertebral endplate, whereby the core does not contact the second boney vertebral endplate.

In one embodiment of the invention, an intervertebral implant includes two conformable endplates. Each endplate includes a material that conforms to a boney vertebral endplate under an anatomical load and a core between the endplates. The core supports boney vertebral endplates between which the conformable endplates have been placed. The position of each conformable endplate is controlled at least in part by the boney vertebral endplate to which it is attached and is independent of the position of the other endplate.

The invention is also directed to a method of replacing an intervertebral disc. The method includes removing at least a portion of an intervertebral disc to form an intervertebral disc space, implanting a first conformable endplate into the intervertebral disc space and in contact with a first honey vertebral endplate. The first conformable endplate is conformable to the first boney vertebral endplate under an anatomical load. A second endplate is implanted into the intervertebral disc space and in contact with a second boney vertebral endplate. A core is implanted between the first conformable endplate and the second endplate, wherein the first conformable endplate partitions the core from the first boney vertebral endplate. The core does not contact the first boney vertebral endplate.

In one embodiment of the invention, the second endplate is conformable to the second vertebral endplate under an anatomical load. Further, the second endplate implanted partitions the core from the second boney vertebral endplate, whereby the core does not contact the second boney vertebral endplate.

In one embodiment of the invention, at least one rigid plate can be implanted between the core and at least one of the first conformable endplate and the second endplate.

The invention has many advantages. For example, the invention provides the boney vertebral bodies from succumbing to device stress shielding, bone remodeling, device subsidence, and device expulsion. Further, the invention also allows for even load distribution across the boney vertebral bodies.

DETAILED DESCRIPTION OF THE INVENTION

The foregoing and other objects, features and advantages of the invention will be apparent from the following more particular description of preferred embodiments of the invention, as illustrated in the accompanying drawings in which like reference characters refer to the same parts throughout the different views. The same number appearing in different drawings represent the same item. The drawings are not necessarily to scale, emphasis instead being placed upon illustrating the principles of the invention.

Figure 1:
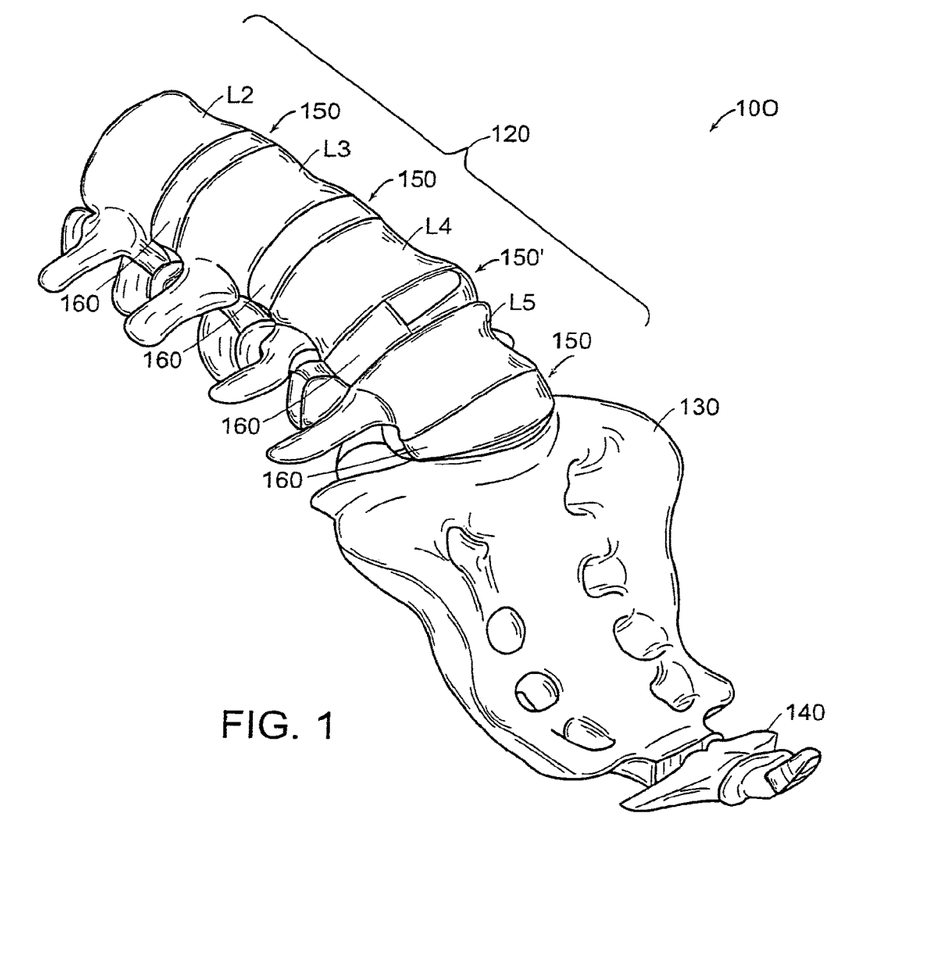
FIG. 1 shows a perspective view of the lower region of the spine in which an intervertebral space has been prepared for implantation of the invention.

The present invention is related to a conformable implant intended to replace an intervertebral disc which has been removed due to disease, infection, deformity, or fracture, for example. FIG. 1 shows a perspective view of the lower region of a human spine 100. This region includes lumbar spine 120, sacral spine 130, and coccyx 140. The lumbar spine 120 is comprised of five (5) vertebrae L5, L4, L3, L2, and L1 (not shown). Intervertebral discs 150 link contiguous vertebra from C2 (not shown) to the sacral spine 130, wherein a single apostrophe (') denotes a damaged disc, such as 150'.

Intervertebral disc 150 includes a gelatinous central portion called the nucleus pulposus (not shown) which is surrounded by an outer ligamentous ring called annulus fibrosus 160. The nucleus pulposus is composed of 80-90% water. The solid portion of the nucleus is Type II collagen and non-aggregated proteoglycans. Annulus fibrosus 160 hydraulically seals the nucleus pulposus, and allows intradiscal pressures to rise as the disc is loaded. Annulus fibrosus 160 has overlapping radial bands which allow torsional stresses to be distributed through the annulus under normal loading without rupture.

Annulus fibrosus 160 interacts with the nucleus pulposus. As the nucleus pulposus is pressurized, the annular fibers of the annulus fibrous prevent the nucleus from bulging or herniating. The gelatinous material directs the forces of axial loading outward, and the annular fibers help distribute that force without injury.

Although the following procedure is explained with reference to the lower spine, the procedure can be performed on any damaged disc of the spine. Further, the following procedure is described with reference to implants. However, it should be understood by one skilled in the art that an implant may be an artificial disc, a spinal fusion cage, or any other device known in the art.

According to one embodiment of the method of the invention, damaged disc 150' is prepared to receive an implant of the invention by removing a window the width of the implant to be implanted from the annulus 160 of the damaged disc 150'. The nucleus pulposus of the disc 150' is removed.

Figure 2:
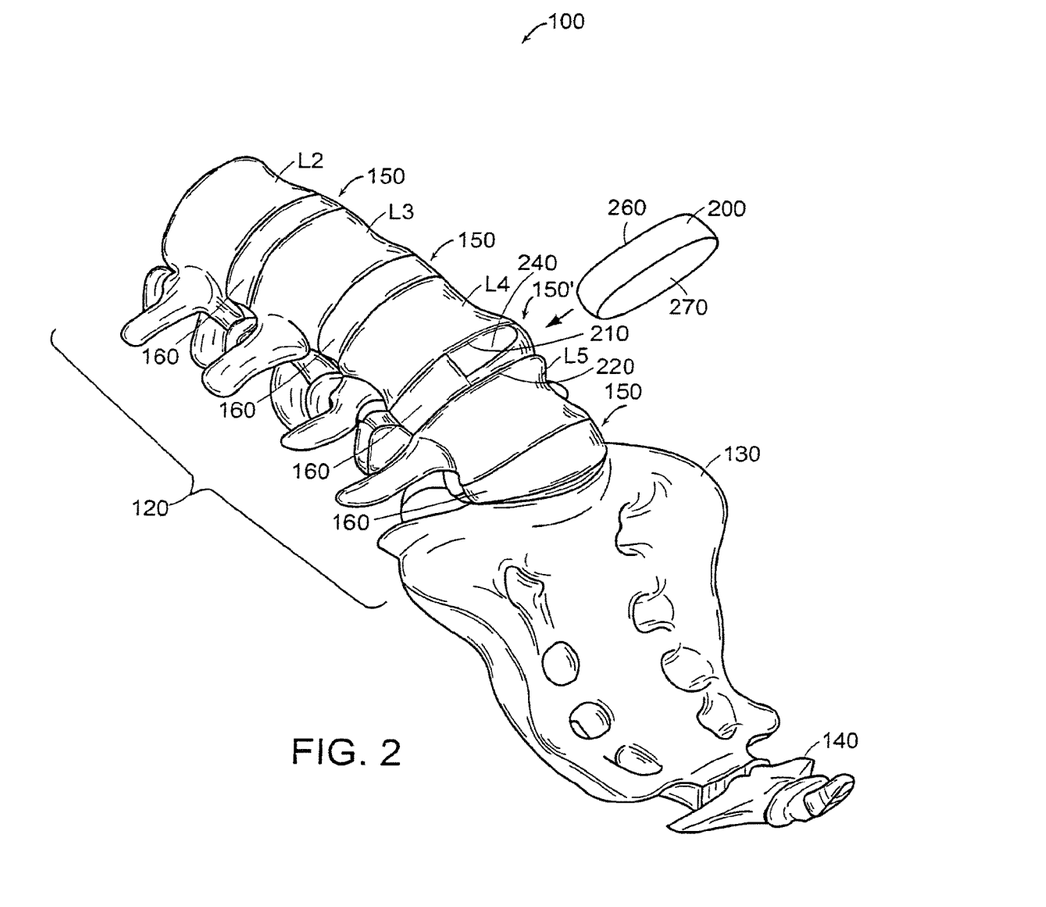
FIG. 2 shows a perspective view of one embodiment of the artificial implant of the invention being inserted into the prepared intervertebral space of the lumbar spine region of FIG. 1.

Referring to FIG. 2, once the damaged disc space is prepared, the surgeon chooses implant 200 of the invention from a kit of implants (not shown). The kit contains pre-fabricated and modular implants of various heights, shapes, and sizes. The surgeon inserts the chosen implant 200 into the intervertebral space 210 located between the superior endplate 220 of the inferior vertebra L5 and the inferior endplate 240 of the superior vertebra L4 (each vertebral body has a superior endplate and an inferior endplate).

The implant 200 may be inserted by hand or with an insertion instrument (not shown). If the implant 200 does not closely match the intervertebral space 210, the surgeon removes the implant 200 and chooses another implant 200 from the kit. This step is repeated until the surgeon determines the implant 200 which closely matches the intervertebral space 210.

The surgeon may then adjust the position of the implant 200 in the intervertebral space if needed. The implant can be adjusted in any direction within the intervertebral space 210. The implant 200 is now ready to be secured to vertebral endplates.

In one embodiment, either superior endplate 260 or inferior endplate 270 of the implant 200 conform to the defined contours (i.e. shapes) of superior or inferior endplates 220, 240, respectively of vertebral bodies under an anatomical load. Preferably, both superior endplate 260 and inferior endplate 270 conform to honey vertebral endplates with which they are in contact. An "endplate" is defined as the portion of the implant that is in contact with a boney vertebral endplate when in use. If one endplate is not conformable to the boney vertebral endplate with which it is in contact, then that endplate can be a rigid material that is suitable for implantation, such as a rigid bio-compatible, metallic, polymeric or biologic material. In one such embodiment, the second endplate and the core are both rigid and, optionally, can be formed of the same material. In still another embodiment, the core and the second, rigid endplate are a single monolith. In the embodiment wherein the second endplate is rigid, the method of the invention can, optionally, include a step of preparing a portion of a second boney vertebral endplate for implantation of the second endplate, such as by grinding or cutting the second boney vertebral endplate. The anatomical load is the weight of the body above the resulting disc space, i.e., the weight of the body above disc space 210 in FIG. 2. In prior art techniques, the superior and inferior endplates of vertebral bodies were shaped to conform to the implants endplates.

The implant 200 can be further secured to the vertebral bodies by attaching at least one protrusion element (360 FIGS. 3B and 3D) to the superior and inferior endplates 260, 270 of the implant 200 to secure the implant 200 to vertebral endplates 220,240. The protrusion element 360 can be a keel, a spike, a tooth, a fin, or a peg.

Figure 3A:
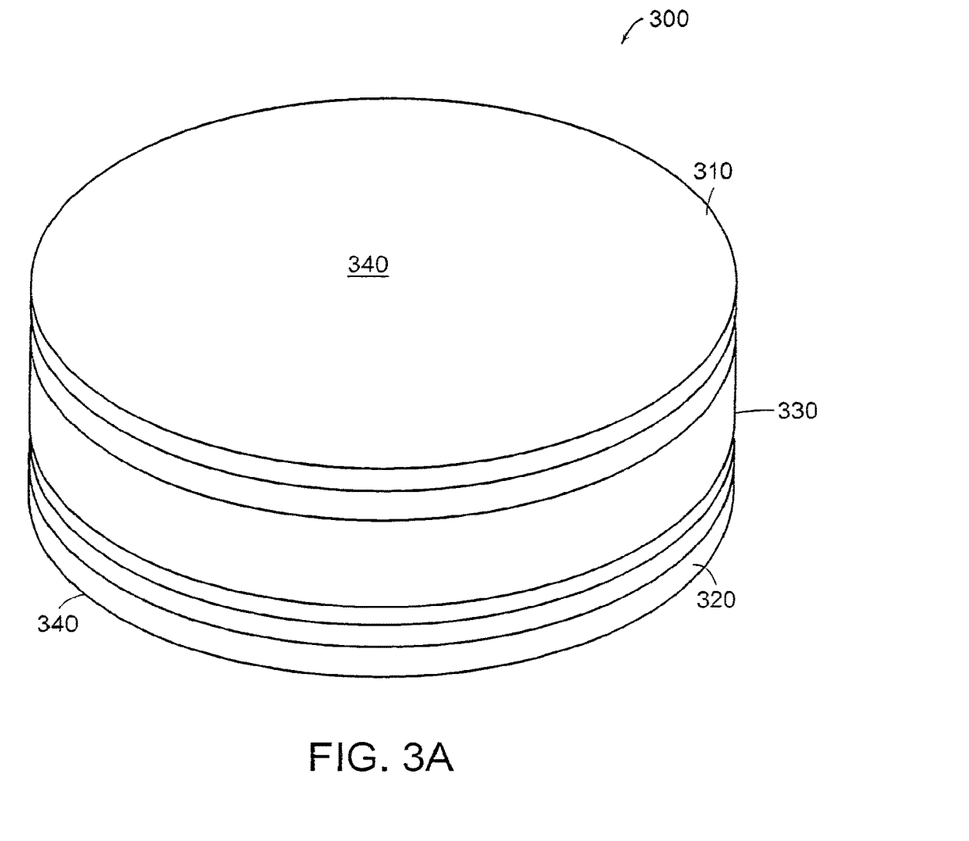
FIG. 3A shows an exploded perspective view of on embodiment of the implant of the present invention.
Figure 3B:
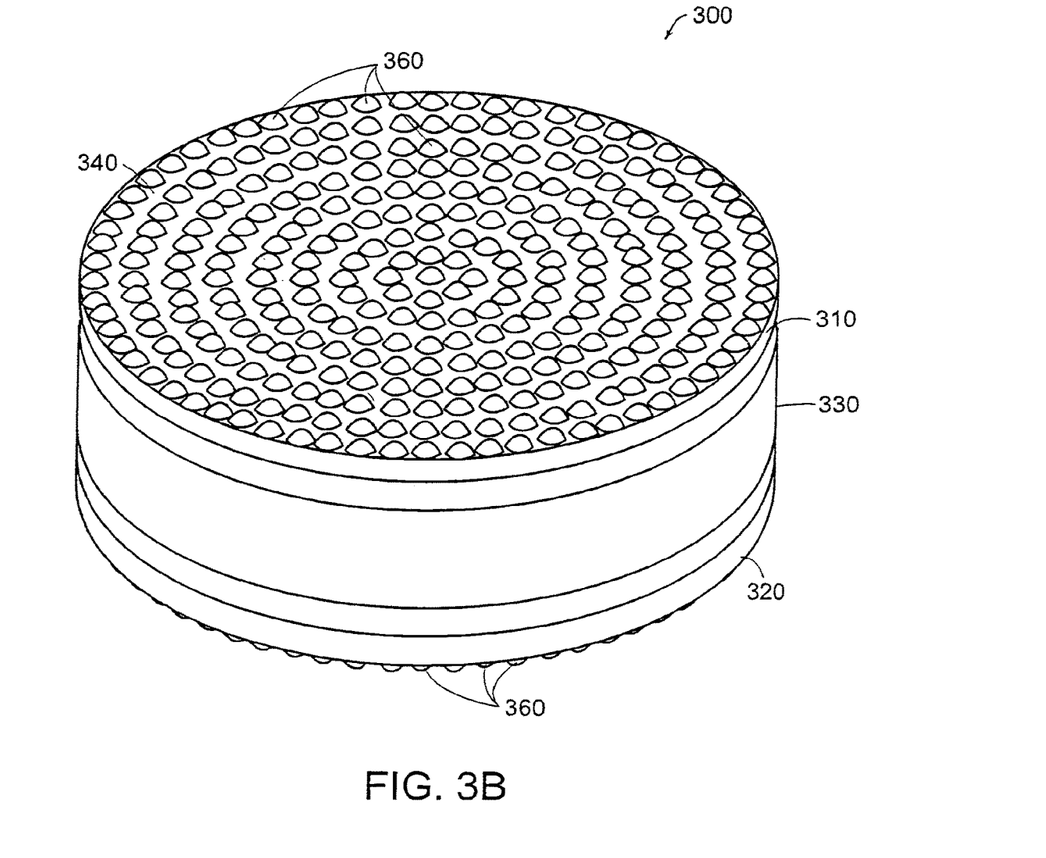
FIG. 3B shows an exploded perspective view of the implant of FIG. 3A with securing elements attached.
Figure 3C:
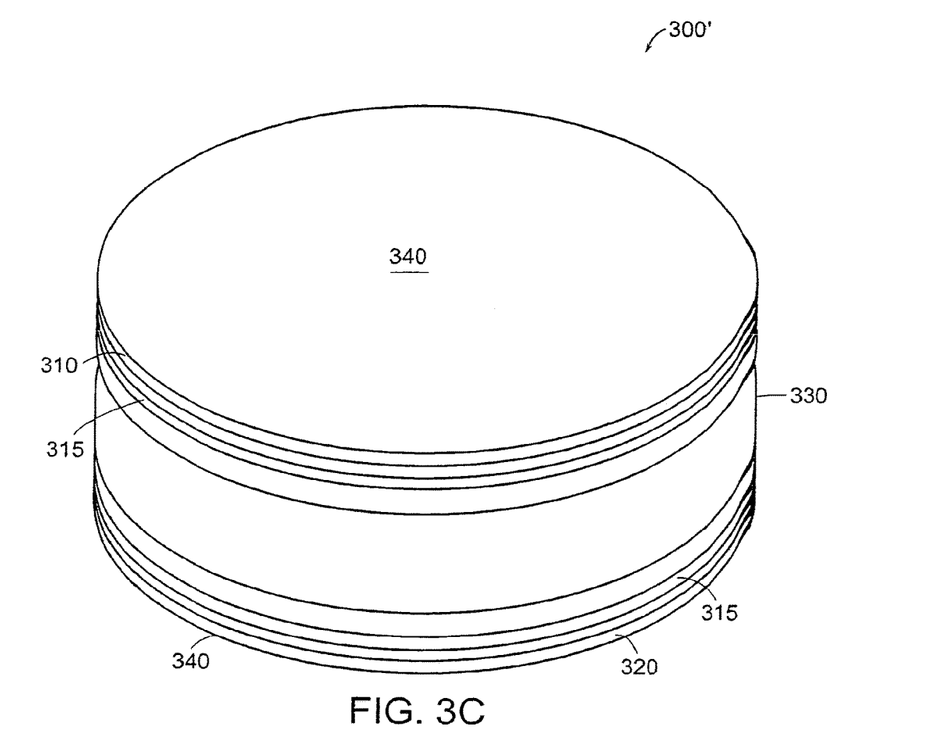
FIG. 3C shows an exploded perspective view of another embodiment of the present invention.
Figure 3D:
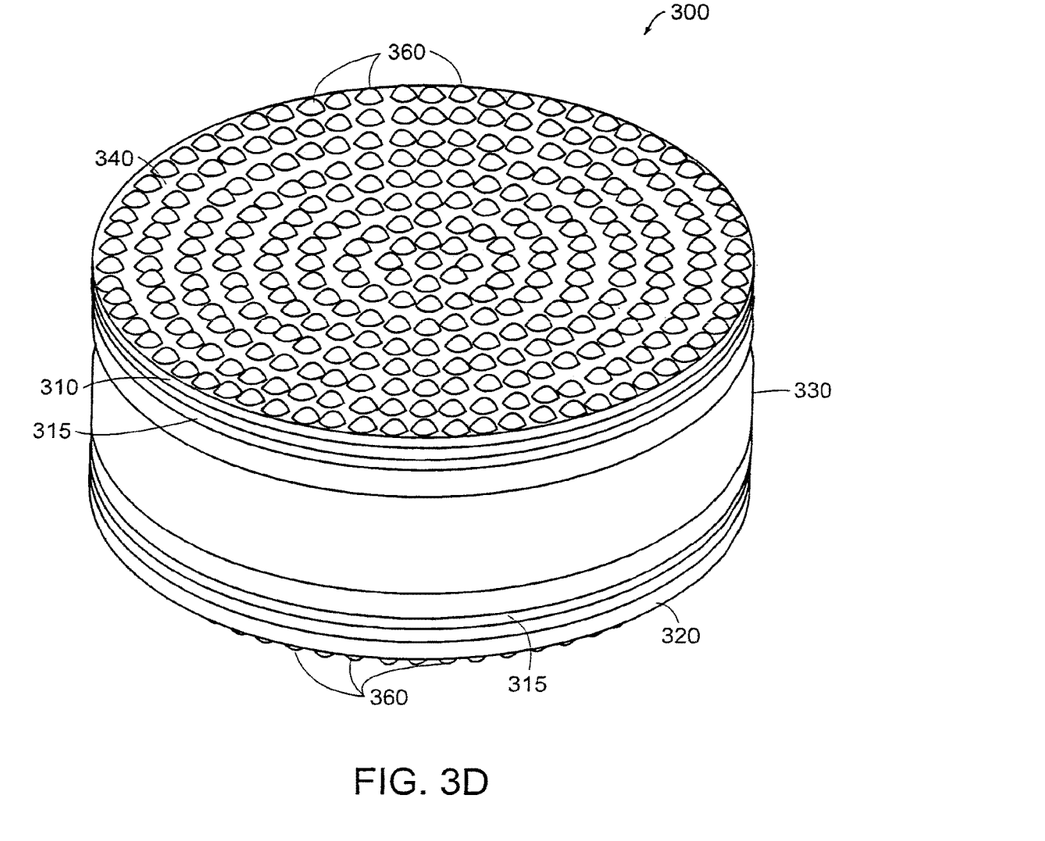
FIG. 3D shows an exploded perspective view of the implant of FIG. 3C with securing elements attached.

FIGS. 3A and 3B show exploded views of a conformable implant 300 of an embodiment of the present invention and FIGS. 3C-3D show exploded views of a conformable implant 300' of another embodiment of the present invention.

Each implant 300, 300' has superior conformable endplate 310, inferior conformable endplate 320, and core 330 disposed between the superior endplate 310 and the inferior endplate 320. Each endplate 310,320 has an endplate surface 340 that is entirely conformable which allows for even load distribution across the boney vertebral bodies. Each endplate 310,320 also partitions the core from boney vertebral endplates contacting surface 340 of each endplate 310,320, whereby the core does not contact the boney vertebral endplates. However, in the embodiment of FIGS. 3C and 3D, a rigid plate 315 which does not deform under an anatomical load can be disposed between each endplate 310,320 and the core 330. It should be understood that a single rigid plate or multiple rigid plates can be used in any combination desired by the surgeon. For example, the surgeon may choose an implant 300' with three rigid plates 315 disposed between the superior endplate 310 and the core 330 while having no rigid endplates 315 between the inferior endplate 320 and the core 330.

Each endplate 310,320 includes at least one member selected from the group consisting of a metallic, polymeric, or biologic material or any combination thereof which conforms to the honey vertebral endplate upon anatomical loading. Examples of these materials include, but are not limited to, titanium, cobalt-chromium, stainless steel, nitinol, polyethylene, polyester, polyurethane, silicone, polycarbonate, collagen, bone morphogenic proteins, demineralized bone matrices, growth factors, or other flexible materials which exceed the yield limit following loading which allows the endplate to conform. The thickness of the material varies depending upon the ductility of the material used, for example, titanium 6-4 can range between 0.0625 mm to 1 mm in thickness, whereas commercially pure titanium can range between 0.0625 mm to 6.35 inches in thickness.

Various methods known in the art can be employed singularly or in combination to help facilitate bone growth into the endplate. For example, each endplate 310,320 can include endplate surface 340 that is textured or roughened, whereby conformable endplate 310,320 bind to honey vertebral endplates upon honey ingrowth of the honey vertebral endplates into textured endplate surface 340 of each endplate 310,320. Examples of a textured or roughened endplate surface include porous beading, hydroxyapatite, and mesh. Further, endplate surface 340 of each endplate 310,320 can be coated with an osteoinductive material. Osteoinductive materials can be metallic, polymeric, ceramic, or biologic materials or any combination thereof. Examples of osteoinductive materials include, but are not limited to, titanium, cobalt-chromium, stainless steel, nitinol, polyethylene, polyester, polyurethane, silicone, polycarbonate, zirconia, alumina, hydroxyapatite, tricalcium phosphate, collagen, bone morphogenic proteins, demineralized bone matrices, growth factors or other materials known to facilitate bone growth.

Protrusion elements 360 can also be attached to the endplate surfaces 340 to provide against disc expulsion. Examples of protrusion elements include keels, spikes, teeth, fins, and pegs.

The core 330 of the implant 300,300' can provide relative movement of the endplates 310,320 about the spine, such as a core in an artificial disc. An example of one such core is described in U.S. Pat. No. 5,401,269, and another example is described in U.S. Provisional Application No. 60/391,845, filed Jun. 27, 2002, the entire teachings of which are incorporated herein by reference. Alternatively, as is the case with a fusion cage, the core 330 of the implant 300,300' can be made from an osteoinductive rigid matrix or cage with struts that are inter-packed with bone to provide short term rigidity and provide for long term ingrowth.

Figure 4A:
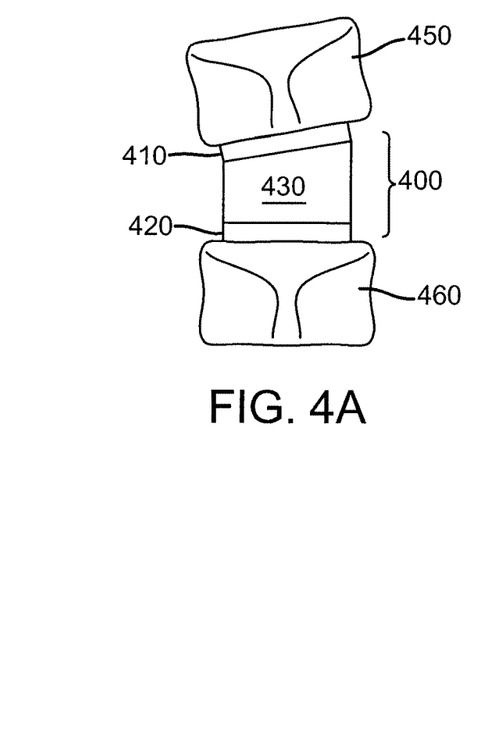
FIG. 4A shows a view of another embodiment of the present invention highlighting movement of spine in relation to the invention.
Figure 4B:
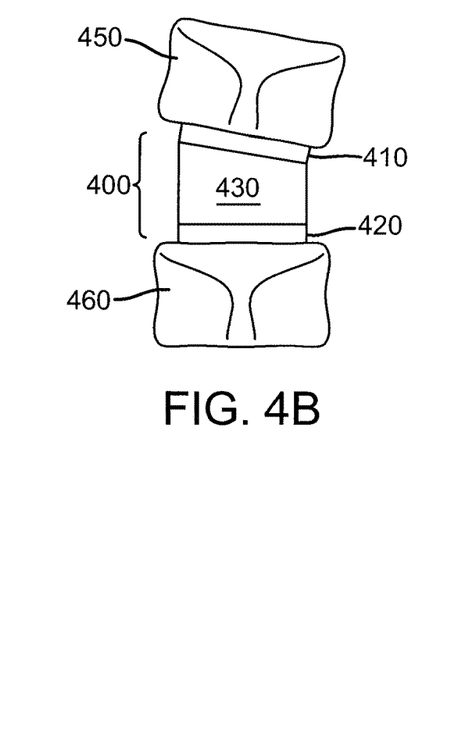
FIG. 4B shows another view of FIG. 4A.
Figure 4C:
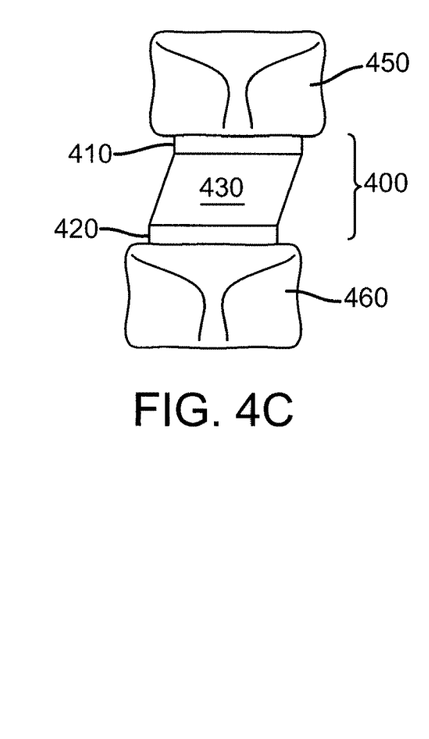
FIG. 4C shows another view of FIG. 4A.
Figure 5:
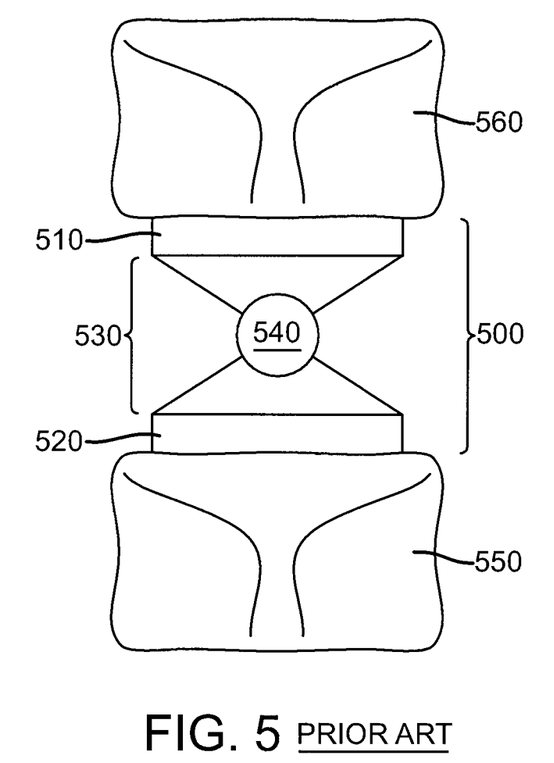
FIG. 5 shows a view of a prior art embodiment highlighting movement of spine about a pivot point.

Referring to FIGS. 4A-4C, in another embodiment of the invention the implant 400 does not have a fixed pivot point within core 430. Each endplate 410,420 of implant 400 moves independent of each other, that is, each endplate 410,420 moves relative to its adjacent boney vertebra 450, 460. The ability for implant 400 not to have a fixed pivot point allows the implant mimic a normal intervertebral disc of the spine. In contrast, prior art implants 500 as shown in FIG. 5 and described in more detail in U.S. Patent Publication 2003/0069642, the entire teachings of which are incorporated herein by reference, have a fixed pivot point 540 at the center of core 530 which does not allow for independent movement of endplates 510,520 relative to its adjacent boney vertebra 550,560.

EQUIVALENTS

While this invention has been particularly shown and described with references to preferred embodiments thereof, it will be understood by those skilled in the art that various changes in form and details may be made therein without departing from the scope of the invention encompassed by the appended claims.

The invention claimed is:

1. An intervertebral implant, comprising:
a first endplate comprising a textured polymeric bone-contacting surface coated with titanium;
a second endplate comprising a textured polymeric bone-contacting surface coated with titanium; and
a core disposed between the endplates;
a rigid plate disposed between the core and the first endplate, the rigid plate configured to partition the core from the first endplate such that the core does not contact the first endplate,
wherein, when the implant is inserted into an intervertebral space between first and second boney vertebral endplates, the first endplate is configured to partition the core from the first boney vertebral endplate such that the core does not contact the first boney vertebral endplate and the second endplate is configured to partition the core from the second boney vertebral endplate such that the core does not contact the second boney vertebral endplate; and
wherein the core is configured to support first and second boney vertebral endplates between which the implant is placed and wherein the implant is a rigid fusion cage.

2. The implant of claim 1, wherein the core comprises a rigid matrix.

3. The implant of claim 1, wherein the core is osteoinductive.

4. The implant of claim 1, wherein the core comprises struts inter-packed with bone.

5. The implant of claim 1, wherein the first and second endplates are conformable to boney vertebral endplates under anatomical load.

6. The implant of claim 1, wherein the entire bone-contacting surface of the first endplate is conformable and the entire bone-contacting surface of the second endplate is conformable.

7. The implant of claim 1, wherein the titanium comprises at least one of a titanium alloy and commercially pure titanium.

8. The implant of claim 1, wherein the titanium has a thickness between 0.0625 mm and 1 mm.

9. The implant of claim 1, wherein the titanium has a thickness between 0.0625 mm and 6.35 inches.

10. The implant of claim 1, wherein the core comprises plastic.

11. The implant of claim 1, wherein the core comprises high density polyethylene.

12. The implant of claim 1, wherein the first and second endplates are separate.

13. The implant of claim 1, wherein the bone-contacting surface of the first endplate extends in a superior direction beyond a superior-most end of the rigid plate.

14. The implant of claim 1, further comprising:
a second rigid plate, the second rigid plate disposed between the core and the lower endplate such that the core does not contact the lower endplate,
wherein each of the first endplate, the second endplate, the first rigid plate, the second rigid plate, and the core form a layer of the implant and each layer has an equal perimeter.

15. A spinal fusion cage, comprising:
a load-bearing core configured to support anatomical loads;
an upper endplate disposed above the core and having a textured polymeric surface coated with titanium;
a rigid plate disposed between the core and the upper endplate, the rigid plate configured to partition the core from the upper endplate such that the core does not contact the upper endplate; and
a lower endplate disposed below the core and having a textured polymeric surface coated with titanium;
wherein the load-bearing core comprises a rigid cage.

16. The fusion cage of claim 15, wherein the upper and lower endplates are conformable to boney vertebral endplates under anatomical load.

17. The fusion cage of claim 15, wherein an entire bone-facing surface of the upper endplate is conformable and wherein an entire bone-facing surface of the lower endplate is conformable.

18. The fusion cage of claim 15, wherein the core comprises struts inter-packed with bone.

19. The fusion cage of claim 15, wherein the titanium comprises at least one of a titanium alloy and commercially pure titanium.

20. The fusion cage of claim 15, wherein the upper endplate, the lower endplate, the core, and the rigid plate each have a perimeter of a same size and shape.

21. A spinal fusion cage, comprising:
a load-bearing core configured to support anatomical loads;
an upper endplate disposed above the core and having a textured polymeric surface coated with titanium;
a rigid plate disposed between the core and the upper endplate, the rigid plate configured to partition the core from the upper endplate such that the core does not contact the upper endplate; and
a lower endplate disposed below the core and having a textured polymeric surface coated with titanium;
wherein the load-bearing core is a rigid matrix.

22. The fusion cage of claim 21, wherein the cage has a single continuous contour formed by the upper endplate, the lower endplate, the core, and the rigid plate.

* * * * *